United States Patent [19]
Dalton

[11] Patent Number: 5,951,512
[45] Date of Patent: *Sep. 14, 1999

[54] INFUSION PORT WITH MODIFIED DRUG RESERVOIR

[75] Inventor: Michael J. Dalton, Evanston, Ill.

[73] Assignee: Horizon Medical Products, Inc., Atlanta, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 08/653,880

[22] Filed: May 28, 1996

[51] Int. Cl.⁶ ................................... A61M 11/00
[52] U.S. Cl. ................ 604/93; 604/890.1; 604/175
[58] Field of Search ................ 604/175, 8–10, 604/212, 93, 51, 52, 236, 237, 905, 246, 890.1, 244, 184, 183, 49, 891.1, 892.1

[56] References Cited

U.S. PATENT DOCUMENTS

| | | | |
|---|---|---|---|
| 3,951,147 | 4/1976 | Tucker et al. | 128/260 |
| 3,971,376 | 7/1976 | Wichterle . | |
| 4,190,040 | 2/1980 | Schulte . | |
| 4,447,234 | 5/1984 | Mayfield | 604/151 |
| 4,464,178 | 8/1984 | Dalton . | |
| 4,468,221 | 8/1984 | Mayfield | 604/152 |
| 4,543,088 | 9/1985 | Bootman et al. . | |
| 4,569,675 | 2/1986 | Prosl et al. | 604/175 |
| 4,673,394 | 6/1987 | Fenton, Jr. et al. . | |
| 4,684,368 | 8/1987 | Kenyon | 604/152 |
| 4,710,167 | 12/1987 | Lazorthes . | |
| 4,710,174 | 12/1987 | Moden et al. . | |
| 4,781,695 | 11/1988 | Dalton | 604/175 |
| 4,886,501 | 12/1989 | Johnston et al. . | |
| 4,892,518 | 1/1990 | Cupp et al. | 604/93 |
| 5,041,098 | 8/1991 | Loiterman et al. | 604/175 |
| 5,041,107 | 8/1991 | Heid, Jr. | 604/891.1 |
| 5,089,016 | 2/1992 | Millner et al. | 623/3 |
| 5,092,849 | 3/1992 | Sampson | 604/175 |
| 5,178,612 | 1/1993 | Fenton, Jr. | 604/283 |
| 5,226,879 | 7/1993 | Ensminger et al. . | |
| 5,263,930 | 11/1993 | Ensminger | 604/93 |
| 5,281,205 | 1/1994 | McPherson | 604/267 |
| 5,328,465 | 7/1994 | Kratoska et al. | 604/93 |
| 5,344,459 | 9/1994 | Swartz | 623/18 |
| 5,562,617 | 10/1996 | Finch, Jr. et al. | 604/93 |
| 5,695,490 | 12/1997 | Flaherty et al. | 604/891.1 |
| 5,702,363 | 12/1997 | Flaherty | 604/93 |
| 5,741,228 | 4/1998 | Lambrecht et al. | 604/93 |

FOREIGN PATENT DOCUMENTS 1280654  2/1991  Canada .

OTHER PUBLICATIONS

Norfolk Medical OmegaPort Access System product brochure; 1 selected page therefrom; 1991.

*Primary Examiner*—Corrine M. McDermott
*Assistant Examiner*—Cris L. Rodriguez
*Attorney, Agent, or Firm*—Needle & Roseberg PC

[57] ABSTRACT

An implantable infusion port which comprises a fluid reservoir with inlet means and outlet means, the reservoir preferably having a toroid-like shape and outlet means directed along a tangent to the reservoir, assures more effective reservoir cleansing when the port is flushed with aqueous saline between uses.

29 Claims, 6 Drawing Sheets

INFUSION PORT WITH MODIFIED DRUG RESERVOIR

This invention is in the field of medical devices which facilitate transmission of fluids transdermally between a container external to a patient's body and a site within the body. More specifically, this invention relates to implanted drug infusion ports, especially to the fluid reservoir element of such ports.

BACKGROUND

It is known in the art of drug therapy to implant an infusion port beneath the skin. The infusion port generally comprises a reservoir, a mechanism for transferring fluid between an external container and the reservoir, and means for transferring the fluid between the reservoir and a site in the body. In one mode of operation, a multidose quantity of a drug is added transdermally to the reservoir component of the implanted infusion port, typically by means of a hypodermic syringe or pump feeding a hollow needle which penetrates the skin and then the wall of the reservoir, most commonly a discrete penetrable area/septum which is part of the wall. The drug is then released slowly from the reservoir via an outlet catheter to the site in the body requiring medication. Using this technique, the drug is supplied to the site relatively undiluted by body fluids and is more effective than if injected intramuscularly or directly into the blood steam.

In a second mode of operation, the implanted infusion port is used to collect various body fluids. In this mode, a syringe generally is employed to draw the desired fluid from the site which lies at the outlet catheter's terminus in the body, through the catheter, into the drug reservoir, through the hollow needle, and into the syringe. Blood samples are commonly collected in this way.

Over the years, a wide variety of implantable infusion ports have been developed and have become the subject of patents. For example, Wichterle, U.S. Pat. No. 3,971,376 describes an implantable capsule with a needle-penetrable wall; the drug reservoir is rounded with no angular relationships between any parts of the reservoir. Schulte, U.S. Pat. No. 4,190,040 discloses an implantable infusion port, the penetrable circular dome of which makes an acute angle against a flat base to create the reservoir. Johnston, et al., U.S. Pat. No. 4,886,501 discloses several implantable devices, the reservoirs of which are cylindrical or conical in shape with walls which angle from a base and a flat penetrable septum at either end thereof.

An infusion port with a cylindrical reservoir which is domed at the septum end thereof but is sealed to create a right angle against a flat base at the other end is described in Dalton, U.S. Pat. No. 4,464,178. Bootman, et al., U.S. Pat. No. 4,543,088 discloses infusion ports with cylindrical reservoirs, the walls of which terminate at one end in a concave septum and make a right angle at the other end against a flat base. Infusion ports with cylindrical reservoirs, the walls of which terminate in right angles against an inlet septum at one end and a base at the other are described in Fenton, Jr., et al. U.S. Pat. No. 4,673,394.

An implantable infusion port in which the fluid reservoir is more or less elliptical but makes an angular seal against a flat penetrable septum region is disclosed in Lazorthes, U.S. Pat. No. 4,710,167, while Moden, et al., U.S. Pat. No. 4,710,174 describes ports with cylindrical or rectangular reservoirs, the walls of which make right angles against bases and penetrable septums at either end thereof. An infusion port with a reservoir, the conical wall of which is sealed at an acute angle against a flat penetrable seal is disclosed in Ensminger, et al., U.S. Pat. No. 5,226,879.

In either operating mode, the infusion port can remain in the body for periods of months to years, and the processes of adding fluids to the infusion port or withdrawing fluid samples therefrom can be carried out numerous times during these periods. Between fluid injections or fluid withdrawals it is standard practice to clean the system by flushing the infusion port with aqueous saline solution. A hypodermic syringe with needle access to the reservoir can be employed for this purpose.

Obviously, if the infusion port is not cleaned effectively between these injections/withdrawals, the internal reservoir of the port can become contaminated and begin to harbor agents of disease. This can lead to problems, such as infection within the fleshy pocket beneath the skin occupied by the infusion port and blood borne infection traveling throughout the body. Such infection can require extensive therapy which may include removal of the infusion port. Currently, there is no practical way to monitor the effectiveness of the cleansing practice while the infusion port is implanted in the body and hidden under the skin.

As a result of investigating the fate of various discarded infusion ports recovered after being implanted and employed in the manner described above for various periods of time, it has been discovered that in almost every case the reservoir contained a deposit of clotted blood and/or drug residue. It is a widely known fact that blood, when allowed to stagnate, will form a cohesive mass or coagulate. This is a natural mechanism to protect the body against excessive bleeding from a wound. Because of the stagnation of the blood which accumulates near the angular junctions and corners in the infusion port reservoir, it coagulates and can become very difficult to flush out. Sophisticated lysing drugs are necessary to dissolve the residue.

In many cases the residue, when cultured, exhibits the presence of bacterial and fungal organisms, such as *Staphylococcus aureus, Staphylococcus epidermidis,* and fungus of the genus Candida. In an attempt to clear the debris which can accumulate, especially at the angular junctions within the reservoir, thrombolytic agents, i.e., agents that dissolve or lyse the thrombosed blood, have been developed. the use of Abokinase® protein lysing agent developed by Abbott Laboratories has been rather successful. The use of such sophisticated materials to remedy what is really an inherent infusion port design problem is expensive and puts the patient at risk of both infection and adverse reactions from the lysing agent.

SUMMARY OF THE INVENTION

Consequently, it is one object of this invention to reduce or prevent the accumulation of undesirable residues in infusion ports. It is another objective to alleviate the residue deposition problem without disrupting currently accepted clinical protocols requiring that infusion ports be routinely flushed with aqueous saline between injections of medication or withdrawals of body fluid. It is another objective to attain these ends by means of simple structural modification of the infusion ports of the prior art. Other objectives will become apparent hereinafter.

All of the infusion ports disclosed in the aforecited prior art, with the exception of the port disclosed in Wichterle '376, employ fluid reservoirs shaped such that there is at least one angular junction between portions of the reservoir. It is believed that such angular junctions decrease the fluid mixing and cleaning or clearing efficiency in the reservoir, especially in the vicinity of such junctions.

Consequently, this invention provides an implantable infusion port which comprises a fluid reservoir, inlet means to access the reservoir, and outlet means from the reservoir, the reservoir having a toroid-like shape, thereby avoiding angular junctions between portions of the reservoir which can lead to eddies, countercurrents and stagnation, creating a more laminar flow pattern within the reservoir, which permits efficient cleaning of the reservoir and other components of the infusion port. In addition or as an alternative to a reservoir having a toroid-like shape, a more laminar flow pattern can be enhanced or created, and efficient cleansing of the infusion port achieved, by directing the outlet means from the reservoir along a line tangent to the reservoir.

DETAILED DESCRIPTION

Figure 1:
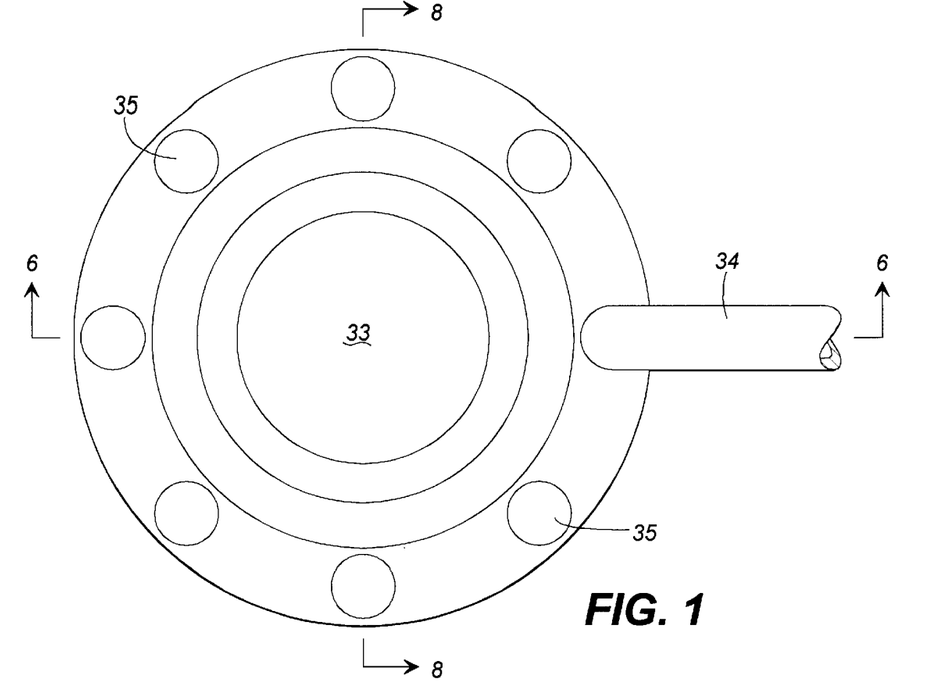
FIG. 1 is an external plan view of some embodiments of this invention.
Figure 2:
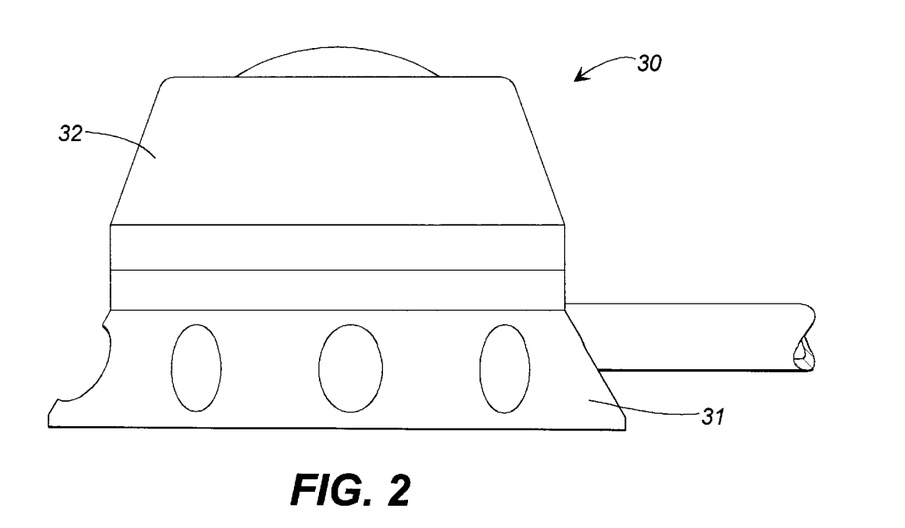
FIG. 2 is an external side view of the infusion port of FIG. 1.
Figure 3:
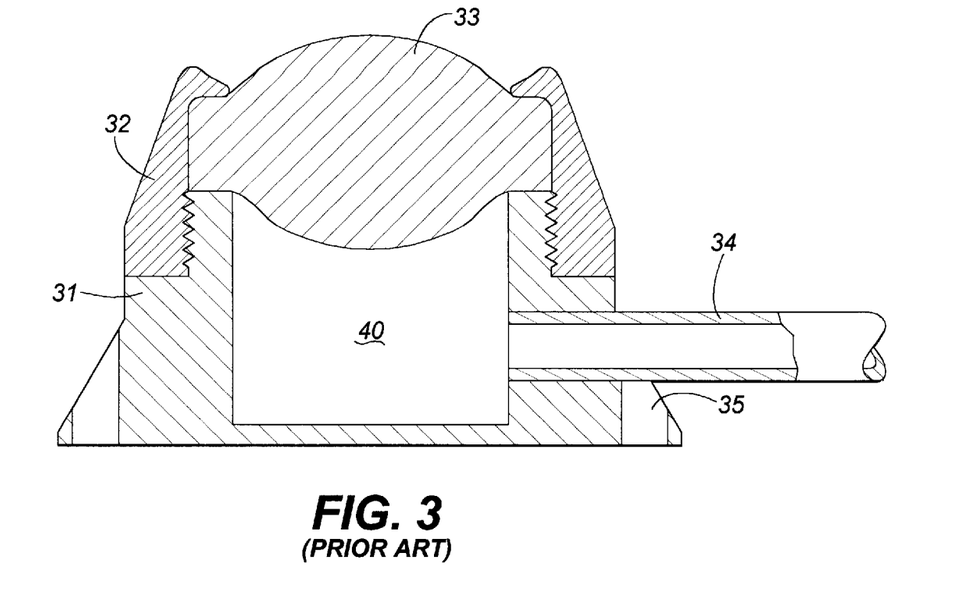
FIG. 3 is an internal view of an infusion port of the prior art in a cross-section comparable to FIGS. 6 and 7.

With reference first to FIGS. 1–3, typical infusion ports 30 of both the prior art and this invention include a reservoir base 31 which generally contains suture holes 35 for fastening the device in the patient's body, inlet means, such as penetrable septum 33, a septum retainer 32 which can be threaded onto reservoir base 31, and outlet means 34, such as a tube for attachment to a catheter.

The inlet means functions to retain the contents of the reservoir within the port but permits the reservoir to be readily accessed by transdermal fluid conduit means, such as a hypodermic needle. In addition to penetrable septum 33, the inlet means can be a rubber valve of the duck bill type which is normally closed and is penetrated to open the closing walls, or a stacked set of slitted elastomeric sheets as described in U.S. Pat. No. 5,226,879, or an elastomeric "O" ring having a normally closed central passage, for example.

It is the function of the outlet means to deliver fluid between the fluid reservoir, shown as element 40 in the Figures, and a specific site in the body. Rather than employing a discrete tube 34 as the outlet means, the reservoir can simply be tapered into a straight outlet stem, e.g., as shown in U.S. Pat. No. 5,226,879, or the taper from the reservoir can be spiraled into a flexible catheter. It will be apparent that other means with similar functional features can also suffice.

As best seen in FIG. 3, a typical infusion port of the prior art includes a reservoir 40 in the shape of a cylinder which terminates in a right or acute angle against septum 33 at one end thereof and in a right angle against reservoir base 31 at the other end thereof.

In general, the structural elements of infusion ports and the interconnections between their various parts, as well as the nature of the materials employed in their manufacture and the techniques for using them, are well known in the art. The rigid parts can be made of plastic or metal, such as titanium, and the elastomeric parts are typically silicone rubber, for example. There are many biocompatible materials that can be used.

According to principles of fluid mechanics, the efficiency of fluid mixing in a container is lower near the walls of the container and especially in any corners where elements of the container wall join together angularly, the more acute the angle, the lower the mixing efficiency. Laminar flow along the walls of the conduit or reservoir enhances the cleaning or clearing of the reservoir. Laminar flow occurs in areas of smooth wall transitions only. Consequently, in the infusion port of this invention, there are no angular junctions between portions of the reservoir; rather, the reservoir is characterized by a toroid-like shape. The smooth transitions between the top and bottom portions of the reservoir enhance the flushing efficiency and fluid dynamics.

Figure 5:
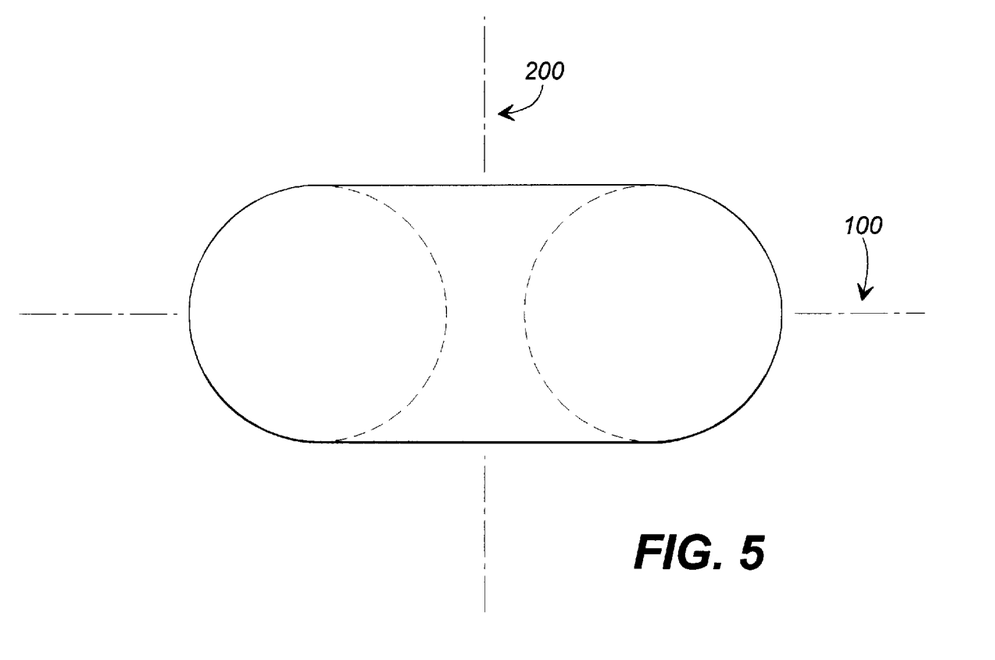
FIG. 5 is a side view of a toroid.

A toroid is the geometric surface generated by a plane closed curve rotated about a line that lies in the same plane as the curve but does not intersect it; a toroid is illustrated in FIG. 5 and is doughnut-shaped. For purposes of this invention, a toroid is characterized by toroidal plane 100 which bisects the doughnut and centralized toroidal axis 200. Plane 100 and axis 200 are perpendicular. In addition, for purposes of this invention, a distinction is made between a toroid-like shape which is "toroidal" and a toroid-like shape which is "quasi-toroidal." In the latter, the geometric surface is generated by rotating a plane unclosed, "C"-shaped curve about a line that lies in the same plane as the curve. These distinctions will become apparent hereinafter.

Figure 6:
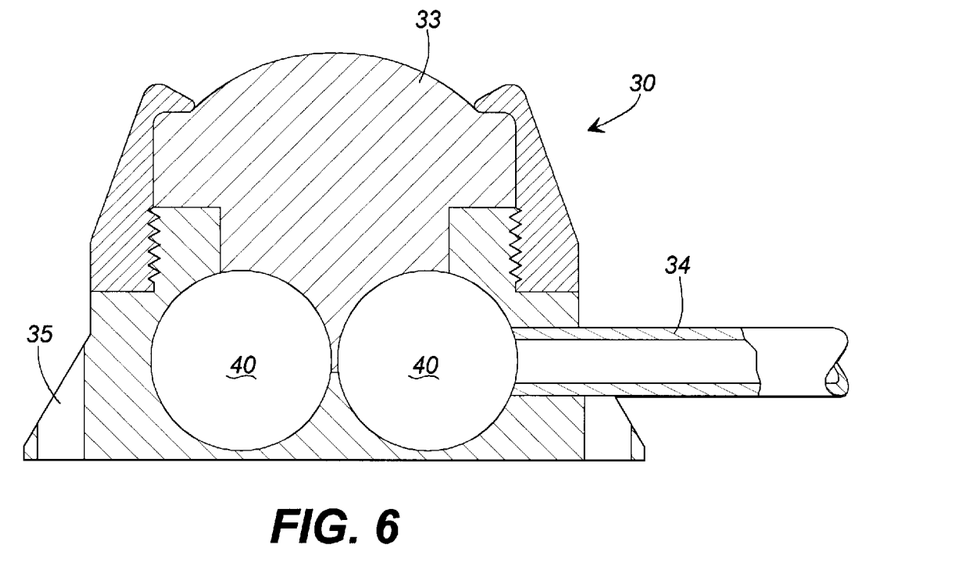
FIG. 6 is an internal view of one embodiment of the infusion port of this invention in a cross-section taken line 6—6 in FIG. 1.

An infusion port of this invention in which toroid-like reservoir 40 is toroidal in shape is illustrated in FIG. 6. Although both lobes of the reservoir are labeled 40 in FIG. 6, it should be understood that the lobes are both part of the same doughnut-shaped reservoir. FIGS. 7–11 show embodiments of the infusion port of this invention in which toroid-like reservoir 40 is quasi-toroidal in shape. As between these two possibilities, a toroid-like reservoir which is toroidal in shape may provide somewhat more efficient mixing, but a reservoir which is quasi-toroidal in shape is easier to manufacture. Furthermore, a toroid-like reservoir with the toroid shape shown in FIG. 6 may occlude a needle which is inserted vertically into the septum at its center, preventing the transfer of fluid to or from the reservoir and requiring needle withdrawal and reinsertion off-center or angled. Consequently, it is preferred that the reservoir be quasi-toroidal in shape as shown in, for example, FIGS. 7–11.

In the embodiments of FIGS. 6–11, inlet means 33 is intersected by the toroidal axis. In the embodiments of FIGS. 6–11, outlet means 34 lies in the toroidal plane.

Figure 7:
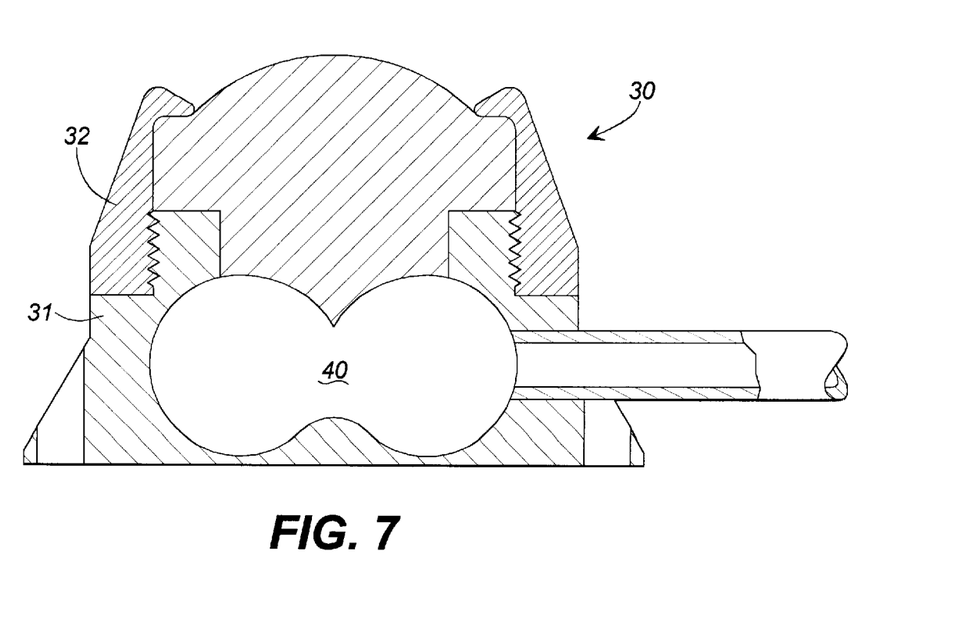
FIG. 7 is an internal view of another embodiment of the infusion port of this invention in a cross-section like FIG. 6.
Figure 8:
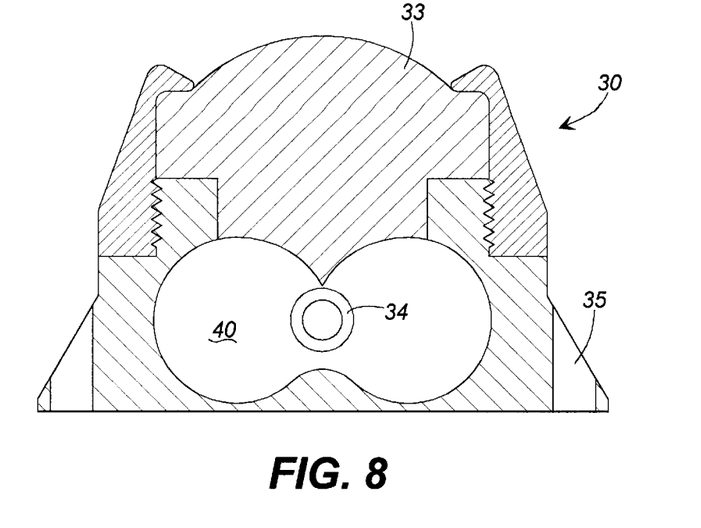
FIG. 8 shows the embodiment of FIG. 7 in a cross-section taken along line 8—8 in FIG. 1.
Figure 9:
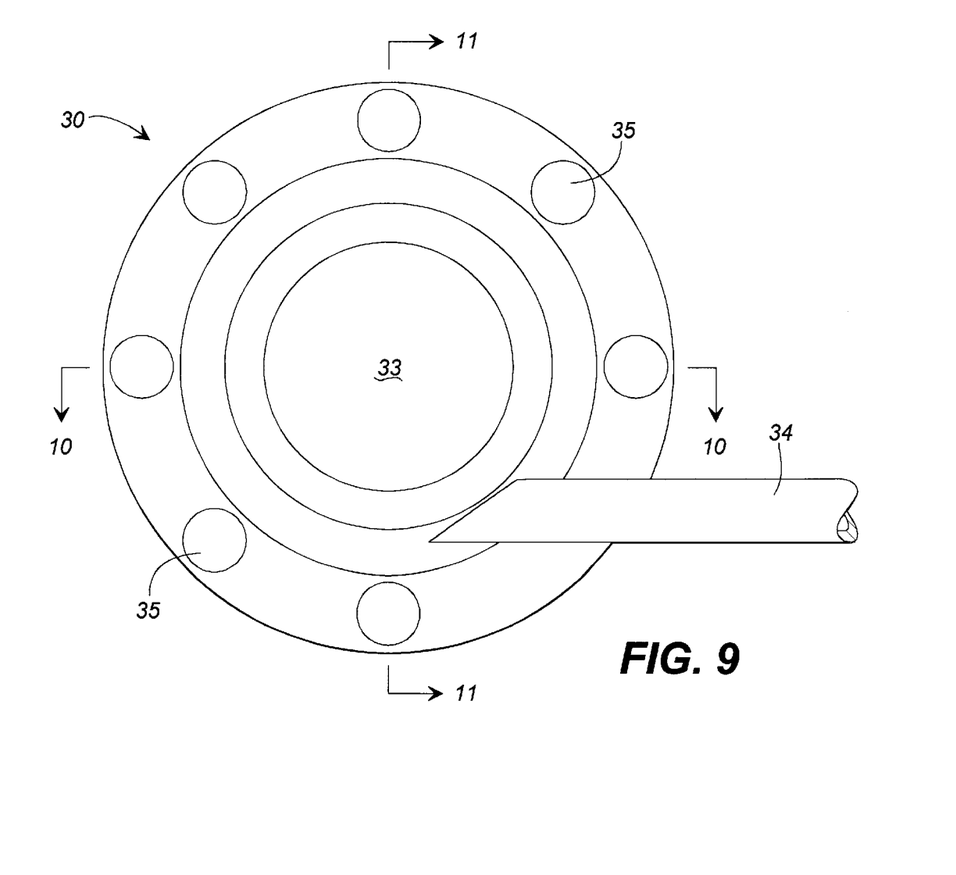
FIG. 9 is a plan view like FIG. 1, but showing another embodiment of the drug infusion port of this invention.
Figure 10:
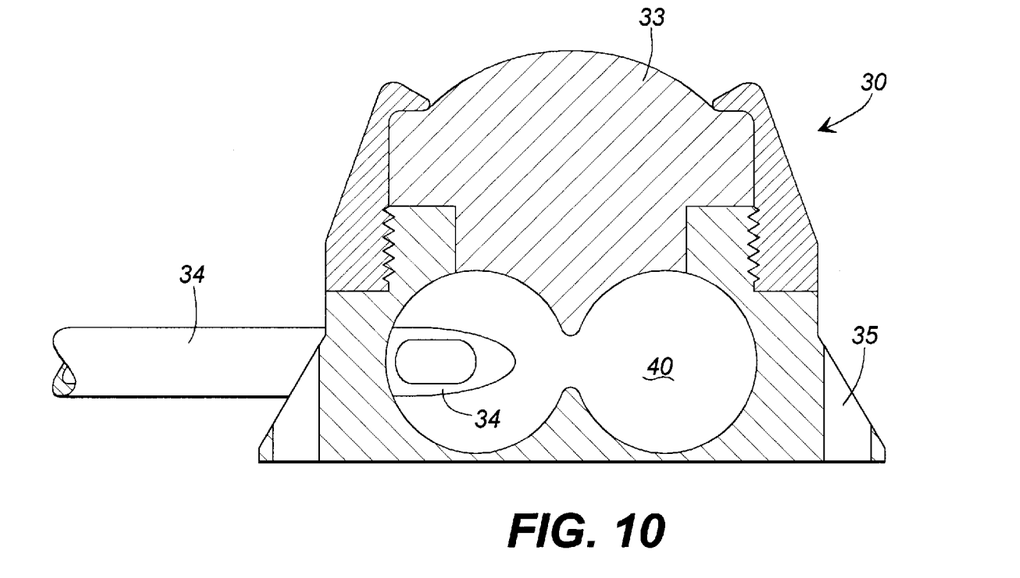
FIG. 10 is a cross-sectional view along line 10—10 in FIG. 9.
Figure 11:
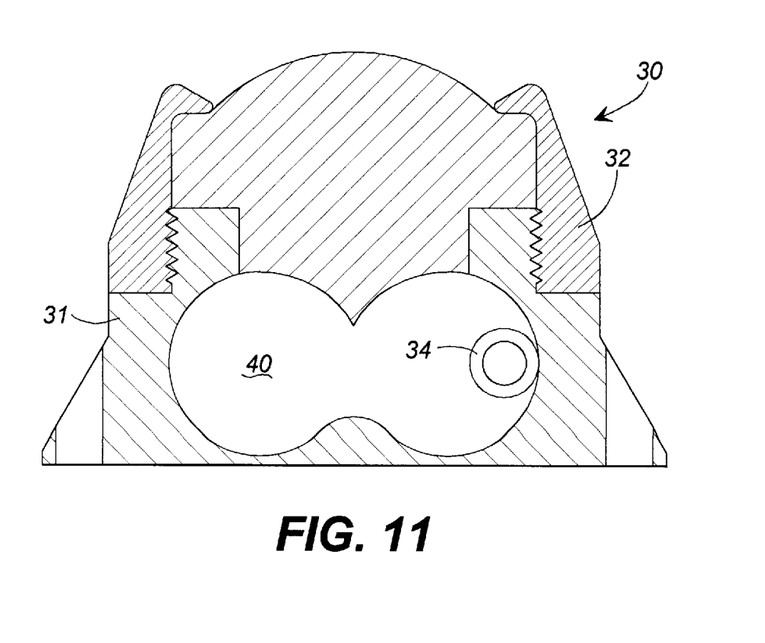
FIG. 11 is a cross-sectional view along line 11—11 in FIG. 9.

A difference which demonstrably does affect the flushing efficiency of the reservoir is illustrated in the embodiment shown in FIGS. 9–11 as compared to the embodiment illustrated in FIGS. 1, 7 and 8. In the embodiment of FIGS.

1, 7 and 8, outlet means 34 is directed along a radius leading to the central axis of circular reservoir 40. On the other hand, in the embodiment of FIGS. 9–11, outlet means 34 is directed along a line tangent to the circular reservoir 40.

The flushing efficiency of the infusion port illustrated in FIGS. 1, 7 and 8 is generally superior to the flushing efficiency of those infusion ports of the prior art with reservoirs having angular junctions such as, e.g., as is illustrated by the cylindrical reservoir 40 in the embodiment of the prior art shown in FIG. 3. The flushing efficiency of an infusion port with a toroid-like reservoir which is also equipped with outlet means directed along a tangent to the reservoir is superior to that of an otherwise identical infusion port with the outlet means directed along a radius of circular reservoir 40. The concept of outlet means being directed along a radius or tangent of a circular reservoir can be generalized readily by those skilled in the art to non-circular reservoirs, qualitatively similar results being expected.

Thus, all else being equal, embodiments with a toroid-like reservoir and also tangential outlet means are especially preferred. It will be evident to those skilled in the art that the flushing efficiency of infusion ports with drug reservoirs which are not toroid-like in shape, i.e., infusion ports of the prior art, will also be enhanced by leading the reservoir outlet means from the reservoir along a line which is tangent to the reservoir. Positioning the outlet means along the tangent whereby the outer wall of the outlet means intersects the outer wall of the reservoir at a point midway between the top portion and the bottom portion appears to be the ideal placement from a fluid dynamics viewpoint. This is illustrated in FIGS. 9 and 10.

Moreover, the invention in which the infusion port reservoir has a toroid-like shape, is not confined to the preferred embodiments shown in FIGS. 7–11, since a number of variations are possible which preserve the toroid-like reservoir shape but in which the other elements of the infusion port are arranged somewhat differently. All of these variations, as well as embodiments with permutations of the elements which are not specifically illustrated, can be expected to exhibit the improved flushing efficiency and ease of cleaning and clearing which characterize this invention.

It will be evident that there are many combinations and possible relationships between the toroid-like reservoir and the reservoir inlet and outlet means. It is to be expected that there will be some differences in the effectiveness of these various embodiments. The particular embodiment to be optimally selected will depend upon the individual circumstances. Although it has been established that orienting the needle for accessing an infusion port parallel to the skin enhances needle stability, it has proved to be extremely difficult to change the habits of health care personnel to access infusion ports "skin parallel" when almost all other skin penetrations are directed perpendicular to the skin. Skin-parallel needle access could readily be provided.

Figure 4:
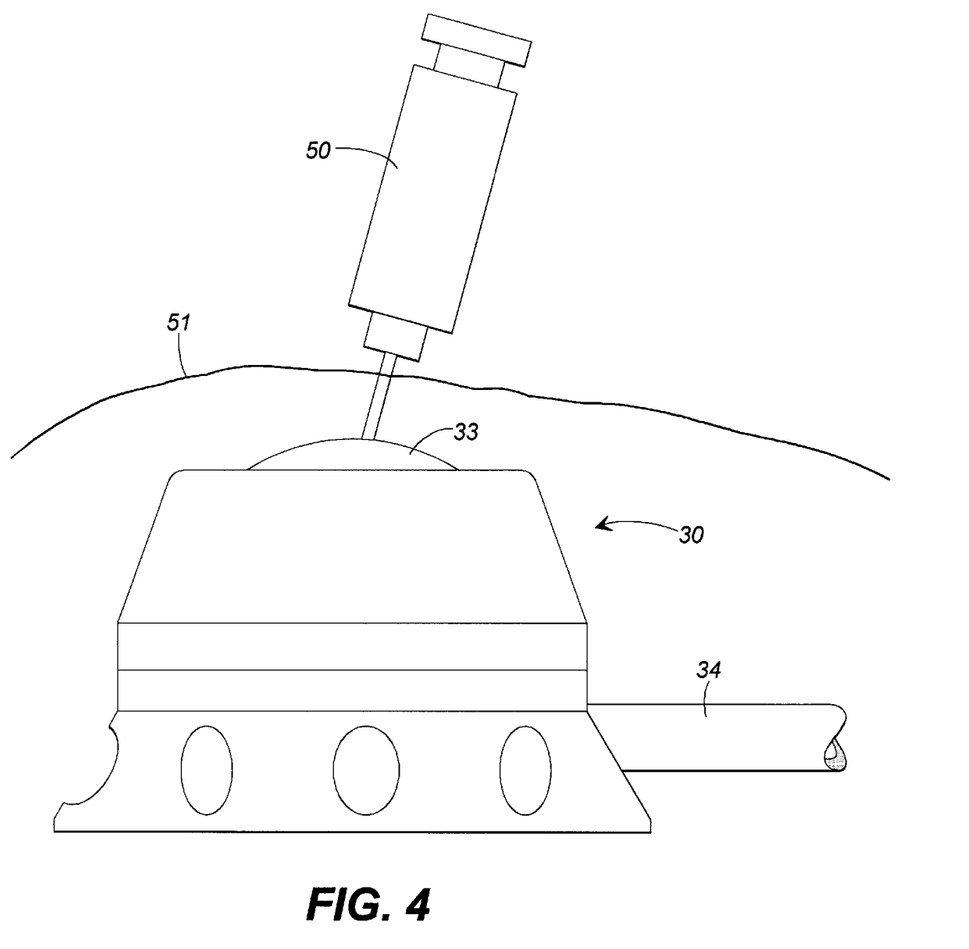
FIG. 4 is a diagrammatic view showing how an implanted infusion port is joined transdermally to an external fluid receptacle and also to a site within a patient's body.

Each of the embodiments of this invention can be employed in a method for accessing a site in a patient's body requiring medication or yielding a fluid to be withdrawn for analysis. FIG. 4 illustrates the manner in which an infusion port 30 of this invention is implanted beneath skin 51 to be accessed through penetrable inlet septum 33 by means of hypodermic syringe 50 in order to supply a drug to or withdraw a fluid sample through outlet means 34 via a catheter connected to or comprising the outlet means. Outlet means 34 can be connected to the patient's venous, arterial or peritoneal system, or a tumor, for example.

The advantages to be realized by implanting a drug infusion port of this invention having a toroid-like reservoir shape and the outlet means directed along a tangent to the reservoir are illustrated in the following Example.

EXAMPLE

Tests were carried out to determine the effect on flushing efficiency of incorporating a reservoir with a toroid-like shape and tangential outlet means into a drug infusion port. The test method employed was referred to in the Port Guidelines published Jan. 31, 1990 by the Chief of the General Hospital and Personal Use Devices Branch of the U.S. Food and Drug Administration.

A solution having a viscosity approximating that of blood was prepared by mixing, by volume, 45 parts glycerol and 55 parts distilled water. While monitoring the electrical conductance of the solution with a conductivity meter (Cole Palmer Mod. #N-014810-00), sufficient sodium chloride was added to increase the conductance of the solution to about 6,660 micro mhos.

Four different drug infusion ports, each equipped with rubber septum inlet means and catheter outlet means were tested.

Ports 1 and 2 had drug reservoirs as shown in FIG. 3 and represent the prior art.

Port 3 is described, as to the inlet means, in U.S. Pat. No. 4,857,053 and also included a cylindrical reservoir with a rounded bottom scooped out of the base.

Port 4 had a toroid-like drug reservoir with tangential outlet means as shown in FIGS. 9–11 of this application.

In each case, the catheter outlet from the port was connected to a flow cell equipped with electrodes for measuring the conductance of the liquid flowing through the cell (Cole Palmer Mod. #N-01481-03). Each infusion port was flushed with the glycerol/water/NaCl solution added by hypodermic syringe through the inlet septum until the conductance of the effluent from the port was about 6,600 micro mhos.

Using a 10 cc hypodermic syringe equipped with a 20 gauge Huber point needle, distilled water having a measured conductance of 0 micro mhos was then added to each infusion port through the septum inlet means, 1 cc at a time. After each 1 cc addition, the conductance of the effluent in the flow cell was recorded. The higher the flushing efficiency of the infusion port's drug reservoir, the less distilled water was required to reduce the conductance of the infusion port effluent to zero.

The test procedure was carried out randomly until each of the infusion ports had been tested ten times. The averaged results appear in the following Table:

| TABLE OF AVERAGED RESULTS | | | | |
|---|---|---|---|---|
| WATER ADDED | EFFLUENT CONDUCTANCE (micro mhos) | | | |
| (cc) | Port 1 | Port 2 | Port 3 | Port 4 |
| 0 | 6790 | 6790 | 6836 | 6838 |
| 1 | 932 | 1234 | 1290 | 1124 |
| 2 | 99 | 117 | 109 | 66 |
| 3 | 28 | 28 | 22 | 14 |
| 4 | 10 | 13 | 10 | 0 |
| 5 | 0 | 1 | 0 | 0 |
| 6 | 0 | 0 | 0 | 0 |

The superiority of Port 4, an embodiment of this invention, is evident.

It is not intended that the scope of this invention be limited to the specific embodiments describe in this specification. The scope is to be limited only by reference to claims:

What is claimed is:

1. An implantable infusion port for transferring a fluid transdermally between an external container and a site within a patient's body comprising
    (a) a reservoir to contain said fluid, said reservoir having a toroid-like shape characterized by a toroidal axis and a toroidal plane;
    (b) inlet means to access said reservoir, said inlet means being intersected by the toroidal axis; and
    (c) outlet means from said reservoir;
    whereby said reservoir can be cleaned efficiently by forcing fluid through said reservoir between said inlet means and said outlet means.

2. An infusion port of claim 1 wherein said inlet means comprises an elastomeric septum.

3. An infusion port of claim 1 wherein said outlet means comprises a catheter to be led to the site in the patient's body.

4. An infusion port of claim 1 wherein said outlet means is directed along a tangent to said reservoir.

5. An infusion port of claim 1 wherein said outlet means is in the toroidal plane.

6. An infusion port of claim 1 wherein said reservoir is quasi-toroidal in shape.

7. An infusion port of claim 1 wherein said reservoir is toroidal in shape.

8. An implantable infusion port for transferring a fluid transdermally between an external container and a site within a patient's body comprising
    (a) a reservoir having a quasi-toroidal shape characterized by a toroidal axis and a toroidal plane;
    (b) a penetrable elastomeric septum inlet to said reservoir; and
    (c) an outlet catheter from said reservoir, said outlet catheter being directed along a tangent to said reservoir to be led to the site in the patient's body;
    whereby the reservoir can be cleaned efficiently by forcing fluid through said reservoir between said septum and said outlet catheter.

9. A method for accessing a site in a patient's body which comprises
    (1) implanting an infusion port beneath the patient's skin, said infusion port including
        (a) a reservoir to contain a fluid, said reservoir having a toroid-like shape characterized by a toroidal axis and a toroidal plane;
        (b) inlet means to access said reservoir; and
        (c) outlet means from said reservoir;
    (2) establishing connection between said outlet means and the site in the patient's body; and
    (3) making transdermal connection between said reservoir and a fluid container external to the patient's body.

10. The method of claim 9 wherein the infusion port inlet means comprises an elastomeric septum.

11. The method of claim 9 wherein the infusion port outlet means comprises a catheter to be led to the site in the patient's body.

12. The method of claim 9 wherein the infusion port outlet means is directed along a tangent to said reservoir.

13. The method of claim 9 wherein the infusion port reservoir is quasi-toroidal in shape.

14. The method of claim 9 wherein the toroidal axis intersects the infusion port inlet means.

15. The method of claim 9 wherein the toroidal plane intersects the infusion port inlet means.

16. A method for accessing a site in a patient's body which comprises
    (1) implanting an infusion port beneath the patient's skin, said infusion port including
        (a) a reservoir to contain a fluid;
        (b) inlet means to access said reservoir; and
        (c) outlet means from said reservoir, said outlet means being directed along a tangent to said reservoir;
    (2) establishing connection between said outlet means and the site in the patient's body; and
    (3) making transdermal connection between said reservoir and a fluid container external to the patient's body.

17. The method of claim 16 wherein the infusion port inlet means comprises an elastomeric septum and the infusion port outlet means comprises a catheter.

18. An implantable infusion port for transferring a fluid transdermally between an external container and a site within a patient's body comprising
    (a) a rigid reservoir to contain said fluid, said reservoir having a toroid-like shape characterized by a toroidal axis and a toroidal plane;
    (b) inlet means to access said reservoir; and
    (c) outlet means from said reservoir;
    whereby said reservoir can be cleaned efficiently by forcing fluid through said reservoir between said inlet means and said outlet means.

19. An infusion port of claim 18 wherein the toroidal plane intersects said inlet means.

20. An infusion port of claim 18 wherein said reservoir is smooth-walled.

21. An infusion port of claim 18 wherein said reservoir is an undivided unitary chamber.

22. An infusion port of claim 18 wherein said inlet means comprises an elastomeric septum.

23. An infusion port of claim 18 wherein said outlet means comprises a catheter to be led to the site in the patient's body.

24. An infusion port of claim 18 wherein said outlet means is directed along a tangent to said reservoir.

25. An infusion port of claim 18 wherein said reservoir has a quasi-toroidal shape.

26. An infusion port of claim 18 wherein said reservoir has a toroidal shape.

27. An implantable infusion port for transferring a fluid transdermally between an external container and a site within a patient's body comprising
    (a) a rigid reservoir to contain said fluid;
    (b) a single inlet means to access said reservoir; and
    (c) outlet means from said reservoir to the site in the patient's body, said outlet means being directed along a tangent to said reservoir;
    whereby said reservoir can be cleaned efficiently by forcing fluid through said reservoir between said inlet means and said outlet means.

28. An infusion port of claim 27 wherein said reservoir is a smooth-walled undivided unitary chamber.

29. An infusion port of claim 27 wherein said inlet is an elastomeric septum.

* * * * *